United States Patent [19]
Nolte et al.

[11] Patent Number: 5,141,713
[45] Date of Patent: Aug. 25, 1992

[54] APPARATUS FOR CONTINUOUS RECOVERY OF CERTAIN ELEMENTS FROM A COMBUSTIBLE LIQUID

[75] Inventors: David G. Nolte, Houston, Tex.; Edwin L. Colling, Jr., Dhahran, Saudi Arabia; Kadry K. Bissada, Bellaire, Tex.

[73] Assignee: Texaco Inc., White Plains, N.Y.

[21] Appl. No.: 769,686

[22] Filed: Oct. 2, 1991

Related U.S. Application Data

[63] Continuation-in-part of Ser. No. 456,713, Dec. 26, 1989, abandoned.

[51] Int. Cl.$^5$ .............................................. B01D 50/00
[52] U.S. Cl. .................... 422/172; 422/189; 422/231; 431/333
[58] Field of Search ............... 422/168, 176, 182, 183, 422/231; 431/260, 262, 168, 169, 263, 333

[56] References Cited

U.S. PATENT DOCUMENTS 3,876,089  2/1975  Germershausen et al. ......... 431/263
4,145,979  3/1979  Lilley et al. ......................... 422/176

Primary Examiner—Robert J. Warden
Assistant Examiner—Krisanne M. Thornton
Attorney, Agent, or Firm—Jack H. Park; Kenneth R. Priem; Harold J. Delhommer

[57] ABSTRACT

A combustion apparatus for continuously obtaining a sample of a preselected trace element contained in a combustible liquid comprising a combustion chamber having inlets for combustible liquid and oxygen, an outlet for gaseous combustion products and a combustion dish, means for continuously supplying oxygen and combustible liquid to the combustion chamber, and a recovery vessel containing a chemical treating solution formulated to recover the preselected element from the combination products.

6 Claims, 1 Drawing Sheet

APPARATUS FOR CONTINUOUS RECOVERY OF CERTAIN ELEMENTS FROM A COMBUSTIBLE LIQUID

BACKGROUND OF THE INVENTION

1. Field of the Invention

This is a continuation-in-part of U.S. Pat. application Ser. No. 456,713, filed Dec. 26, 1989. This invention relates to an apparatus for the recovery of certain elements from a combustible liquid. More particularly, the invention concerns a continuous combustion apparatus for recovering in quantity the trace amounts of certain elements, such as iodine, present in crude oils.

2. Background

The age of orude oil found in a region is a significant parameter.in deciding where next to explore for crude oil in that region with a reasonable prospect of success. The age of the oil establishes a relationship between the oil and a possible source rock, i.e. where the oil potentially originated, as compared to where it was actually found since oil, being fluid, will migrate when certain geological conditions are present. Once the likely source rock is established, this is a factor in deciding where next to drill.

One of the methods of determining the age of crude oil is to use iodine-dating. Iodine is found in crudes in small, trace quantities. The radioactive isotope of iodine decays with time at a known rate to a stable, non-radiooactive isotope. The relative concentration of isotopes provides a basis for estimating the age of the crude oil. Thus, in order to measure or estimate crude oil age, it is essential to collect a sufficiently large sample of iodine from the crude oil to be abl to determine the relative quantities of iodine isotopes present with a reasonable degree of accuracy.

The existing chemical methods for recovering iodine from crude oil are complex, lengthy, tedious and require the attention of skilled chemists. These processes include such chemical means as liberating organically bound iodine by reaction with biphenyl sodium or complexing the iodine with mercury.

More recently, combustion techniques have found use in recovery of iodine and other elements from combustible compositions such as crude oil and coal. An article entitled "Determination of Volatile Elements in Coal and Other Organic Materials," *American Laboratory*, August, 1981, explains how to use a combustion bomb, the "Parr bomb," to analyze for specific elements present in the composition burned. The method involves the burning of a sample in a pressurized oxygen atmosphere within a closed vessel which retains all the combustion products. The organic compounds are oxidized to carbon dioxide and water, while other volatile gaseous elements are absorbed in water placed in the bottom of the bomb. This solution then can be analyzed for specific elements. The Parr oxygen bomb has also been used to determine t elements such arsenic, mercury, phosphorous, selenium, boron and some other trace elements.

The use of oxygen bombs, such as the Parr bomb, is well-known to those of ordinary skill in he art of the analysis of crude oils for iodine and other elements and is described in the ASTM Standards at ASTM 144-64 (reapproved 1981). The manufacturer of the Parr bomb, the Parr Instruments Company of Moline, Ill., publishes literature describing the various models of Parr bomb and their methods of use. However, Parr's largest commercial bomb has only a 10 gram capacity so that, if an element desired to be liberated is only present in trace amounts, then several thousand combustions and recoveries of the element.must be performed.

Parr bomb combustion techniques generally entail placing small quantities of oil, about 10 grams, in a sealed vessel along with 10 grams of water and about 1 ml of 1 molar sodium bisulfite. The vessel is then charged with several hundred pounds per square inch of oxygen and the oil is ignited. When combustion is complete, the vessel is cooled so that substantially all the water inside condenses. Some of the liberated iodine then enters the water solution by diffusion and reacts to form a salt. When the vessel is opened, any undissolved iodine, which often comprises up to about 50% of the iodine, escapes along with the products of combustion.

This procedure is time consuming and requires the use of relatively expensive laboratory manpower to perform the repetitive tasks of loading the bomb, combustion, cooling and recovery of the dissolved element. Further, the Parr bomb generally suffers from the disadvantage that recovery of the iodine liberated by combustion is not substantially complete—a large proportion of iodine is unrecovered and lost in the escaping gaseous combustion products. This inefficient recovery of iodine contributes to the number of batches of crude oil that must be burned to obtain a sample of iodine large enough for reliable analytical testing to determine the age of the crude oil.

The Parr bomb batch size cannot safely be increased beyond the 10 grams stipulated because O-rings used to seal the bomb once it is loaded tend to weaken as a result of the heat generated by combustion. This often results in leakage and loss of the combustion gases and the liberated iodine.

The concurrently used combustion techniques therefor suffer from several inherent disadvantages. Firstly, large amounts of oil must be incinerated in small batches in order to recover detectable amounts of the sought-for element. For example, it may be necessary to burn as much as about 100 liters of oil to recover sufficient iodine for testing. Given the small maximum size of the combustion bombs, the production of such a quantity of iodine may require several months. However, in many instances, time is of the essence. It is therefore desirable to develop a process which does not require such lengthy time delays. Secondly, the capture of iodine by diffusion into water is inefficient. A relatively high proportion of the iodine liberated is lost with the escaping combustion gases when the vessel is opened. It would be desirable to develop a fast, easy to operate, safe process which allows the recovery of a high proportion of the liberated iodine.

SUMMARY OF THE INVENTION

The invention is an apparatus for the combustion of liquids in the recovery of a preselected element from gaseous combustion products, said preselected e ements selected from the group consisting of iodine, arsenic, mercury, phosphorous, selenium and boron, comprising a combustion chamber having an inlet for oxygen, an inlet for combustible liquid, and an outlet for gaseous combustion products produced in the combustion chamber, said outlet in flow communication with a recovery vessel containing a chemical treating solution formulated to recover a preselected element from gaseous combustion products, a means for continuously supplying oxygen, a means for continuously supplying a combutible liquid to the combustion dish, and a means for intimately contacting the gaseous combustion products with the chemical treating solution to recover into the chemical treating solution the preselected element. The oxygen supplying means is in flow communication with the combustion chamber and combustion zone. The liquid supplying means is in flow communication with the inlet for combustible liquid and the combustion dish. The means for intimately contacting the gaseous combustion products with the chemical treating solution is in flow communication with the recovery vessel.

The combustion chamber comprises a combustion dish in flow communication with the inlet for combustible liquid and constructed so as to provide the combustible liquid to a combustion zone within the dish. The combustion chamber also comprises a means for igniting combustible liquid within the combustion zone to produce gaseous combustion products of the combustible liquid.

DETAILED DESCRIPTION OF THE DRAWINGS

DETAILED DESCRIPTION OF THE PREFERRED EMBODIMENT

Figure 1:
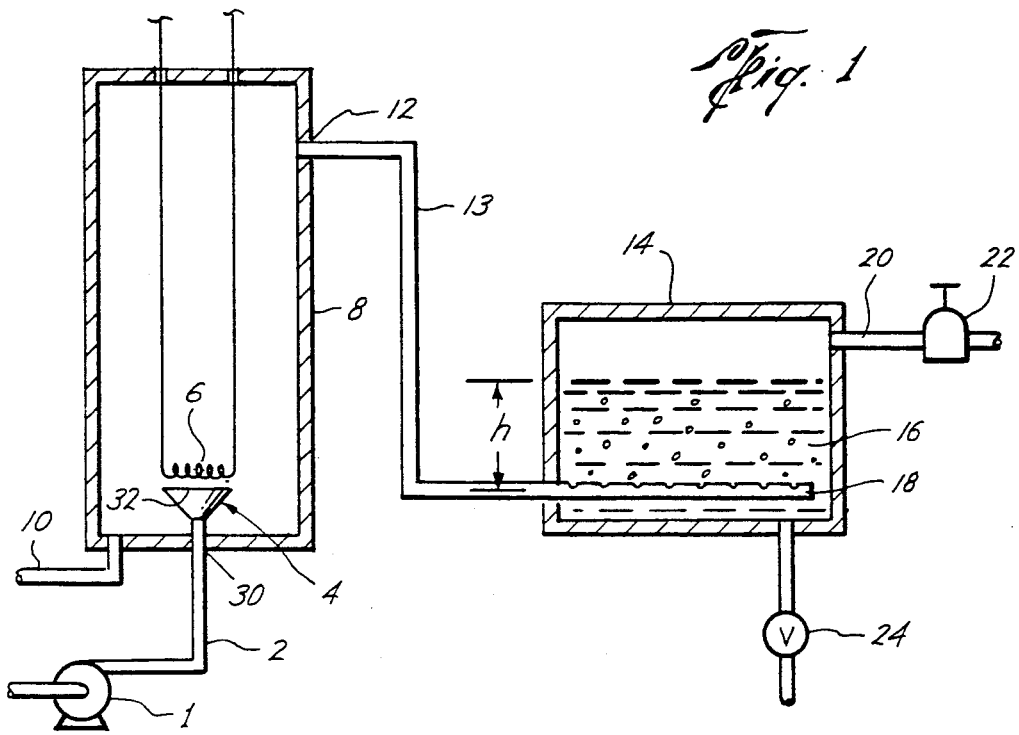
FIG. 1 is a diagram schematically showing the essential components of the invention apparatus.

In marked contrast to prior art batch combustion processes, the apparatus and process of the invention are designed for continuous operation. Thus, for instance, crude oil is continuously pumped into a high pressure combustion vessel which is continuously purged with oxygen or an oxygen-rich gas mixture able to support combustion. The pump oil flows upwardly into the combustion vessel through a combustion dish. The oil is then ignited by an ignition means, such as for instance, a hot wire.

Once combustion is initiated, the level of oil in the combustion dish drops thereby reducing the burning surface area or "the flame front" until the rate of burn-off is in equilibrium with the rate at which the oil is pumped into the combustion chamber. At this point, the combustion process is at steady state.

Gaseous combustion products including the preselected element or elements are diverted to a recovery vessel fitted with a sparger. The gaseous combustion products including the element exit from the sparger and are intimately contacted with a chemical treating solution which is able to recover the preselected element or elements from the combustion gases.

To recover iodine, the chemical treating solution could be an acidified solution of sodium bisulfite or other chemicals known to enhance iodine dissolution. It may also be possible to collect iodine in acidified water and later treat the water with sodium bisulfite or a similar compound to recover iodine. Other chemical treating solutions to recover elements other than iodine may be devised by those skilled in the art. The undissolved combustion gases exit from the recovery vessel through a back pressure regulator which controls the system pressure.

When a sufficient quantity of the preselected element has been recovered, the process is safely terminated by turning off the oil pump thereby removing the fuel for combustion. The preselected element is then recovered from the chemical treating solution by known analytic chemical techniques such as precipitation. Alternatively, the chemical treating solution may be analyzed in order to determine the quantity of the preselecte element present in the combustible liquid.

The invention apparatus and process provide a means for rapidly and efficiently obtaining a usefully sized sample of an element or oxide of the element that is present in smal quantities in a combustible liquid. Thus, the invention apparatus and process has broad application, but is particularly suited for the recovery of trace elements such as iodine from crude oil.

The description of the apparatus and process that follows relates in particular to iodine recovery from crude oil, but could be applied generally to recovery of many desired elements from a combustible liquid.

Crude oil is pumped via pump 1 through the inlet for a combustible liquid or conduit 2 into the base or inlet 30 of a funnel-shaped combustion dish 4. A means for igniting the combustible liquid or crude oil, in this instance a hot wire 6, is positioned so that it can be used to ignite the crude oil held in the combustion zone 32 of the combustion dish 4. The dish 4 is enclosed in a high pressure combustion chamber 8 which is equipped with one or more inlets for oxygen 10 and an outlet for gaseous combustion products 12. Oxygen is supplied to the combustion chamber 8 under pressure and the crude oil is ignited in the combustion dish 4.

Combustion gases including the preselected element or elements exit via outlet 12 through conduit 13 and are carried to the recovery vessel 14. Conduit 13 may optionally be fitted with surrounding cooling coils or other means to cool the combustion gases, although preferably not to a temperature at or below the dew point of the gases. Recovery vessel 14 is at least partially filled with a chemical treating solution 16 containing a chemical reagent able to enhance the solution of the preselected element in the treating solution 16. The combustion gases ar intimately contacted with the chemical treating solution 16, for instance by passing the gases through a sparger 18. This serves to break the gas stream into finely-divided bubbles thereby providing a high surface area to volume ratio which improves contact between gas and liquid and facilitates the mass transfer of the preselected element into the chemical treating solution 16. The combustion gases, scrubbed of the preselected element, exit from the recovery vessel 14 via scrubbed gas outlet 20 at rate controlled by a back pressure regulator 22. When sufficient preselected element has been collected, the chemical treating solution may be withdrawn from the recovery chamber through draw off valve 24.

Pumping rates, oxYgen flow rates and the like depend upon the size of the equipment. Thus, larger equipment will clearly require higher crude oil and oxygen flow rates. it is, however, preferred that the oxygen pressure be maintained in the range 50 to 200 psig, more preferably about 150 psig, to ensure complete combustion as determined by a minimal or zero level of carbon monoxide in the exiting combustion gases. A carbon monoxide analyzer may be used to analyze the combustion gases. When carbon monoxide is detected, the oxygen rate which may be measured, for instance by an in-line rotameter, may be increased until the level of carbon monoxide is reduced to substantially zero.

Combustion generates a great deal of heat and this heat may be removed by providing a means for cooling the combustion chamber such as by submerging the combustion chamber at least partially in water or surrounding it with a water or glycol jacket. Water flow through the water bath or jacket may be controlled so that the wall temperature of the combustion vessel in the flame region is preferably maintained at or less than about 125° C. Thermocouples may be inserted into the combustion chamber to measure the wall temperature in this region and preferably also at another point above the flame region.

If flame temperature and interior combustion chamber temperature gets too high, a coking of crude oil (combustible liquid) may occur in the combustion dish or burner hindering effective combustion and throughput. In addition to cooling the chamber, heat may be controlled by moving excess gasses in and out of the combustion chamber.

In the recovery of the preselected element from the combustion gases, it is preferable to provide some means for intimately contacting the gases with the chemical treating solution. While this may be achieved through elaborate scrubbers such as packed columns, wherein the gaseous combustion products containing the preselected element to be scrubbed enter at the bottom and flow countercurrent to the chemical treating solution entering through the top of the scrubber, a simple device such as sparger will usually suffice. In order to use a sparger, it is essential to ensure that the combustion products gas stream is broken into small bubbles to allow intimate contact between gas and lqiuid. It is also necessary to provide a sufficient depth, h, of chemical treating solution so that the bubbles travel a path sufficiently long to enable substantially complete mass transfer of the desired element into the solution. This depth may be readily determined by initial calculations of a type known to those skilled in the art based upon the diffusion coefficient of the gaseous element it is desired to recover in the specific chemical treating solution, where such data is available. Alternatively, or as a supplement to such calculations, simple experimentation not involving undue effort will determine the optimal depth, h, for a particular chemical treating solution and combustion gas combination.

In the recovery of iodine from crude oil, it has been found that when the chemical treating solution is a 1M sodium bisulfite solution acidized with sulfuric acid, then a liquid depth of only about 3-4 inches is needed to remove substantially all the iodine from the stream of combustion gas. This is a significant improvement in recovery when compared to the typical recovery of about 50% obtained with Parr bombs.

Since the combustion chamber, the recovery vessel and conduits connecting these components will be under pressure, the equipment should be designed in accordance with good engineering practice to withstand this pressure and also the heat generated by combustion. As previously mentioned, cooling means such as cooling coils surrounding conduit 13 may be used to minimize the quantity of water evaporated from the chemical-treating solution in the recovery vessel. These cooling coils are especially useful if it is desired to operate the apparatus for a lengthy period of time such as may be necessary when the preselected element is only present in trace amounts in the combustible liquid.

Depending upon the throughput, i.e. combustion rate of the combustible liquid, a commercial or custom built burner may be used to effect combustion. The burner may be a combination combustion dish and ignition means within the combustion chamber. However, in most instances for lab-scale applications, the throughput will be too low to use commercially available burners. Consequently, the apparatus of the invention provides a unique combustion dish which allows the rate of combustion to equilibrate to a rate equal to the rate of combustible liquid supply.

Figure 2:
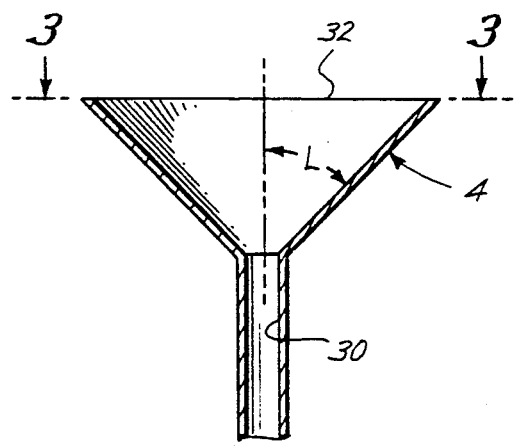
FIG. 2 is a elevation view taken partly in cross-section of a typical combustion dish.
Figure 3:
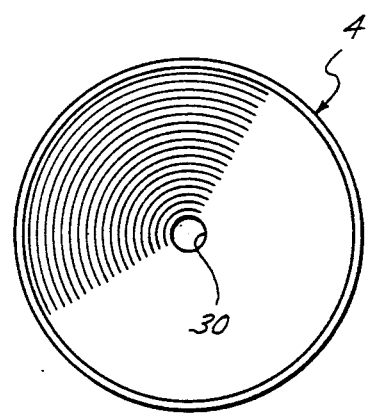
FIG. 3 is a view taken along the line 3—3 of FIG. 2.

The combustion dish of the present invention should preferably be sized to hold about the maximum volume of combustion liquid that will be pumped in one minute. The funnel-shape exemplified in FIG. 2 is designed to ensure that, once ignited, the flame front will automatically adjust so that the rate of combustion is equal to the rate at which the combustible liquid is fed to the combustion dish. To achieve this, the included angle, 2L, of the funnel should be sufficiently large to allow rapid equilibration of the flame front position. Thus, the included angle may vary from about 90°-160° (dish sides angularly sloped between about 90° and about 60°) and should preferably be in the range of about 110°-130°.

While the dish, whioh is preferably the same as or machined into the bottom of the combustion chamber, has a circular plan view as shown in FIG. 2, other shapes and designs are also useful provided that as the combustible liquid flows further from the inlet into the combustion zone 32, the surface area of the combustible liquid exposed to oxygen increases. Thus, in the funnel-shaped dish of FIG. 2, the exposed surface area of the combustible liquid increases as it flows from inlet 30 to combustion zone 32. The combustion zone 32 encompasses an upper area of the combustion dish 4 wherein combustion takes place. The combustion zone 32 will vary in size according to the flow rate of the combustible liquid, the shape of the combustion dish and other factors.

As a variant of this design, the funnel-shaped dish could for instance, be inverted to provide a volcano-shaped or inverted funnel-shaped dish with combustible liquid supplied to the volcano tip and overflowing down the external sides of the inverted funnel-shaped dish. Thus, the combustible liquid will expose an increasing surface area to oxygen when the liquid supply rate is increased thereby causing a higher rate of combustion. Consequently, the rate of liquid combustion will equilibrate to the rate of liquid supply, provided that the supply does not exceed the surface area capacity of the particularly combustion dish.

In the specification and claims the term "preselected elements" includes the defined group of chemical elements, such as iodine, arsenic, mercury, phosphorous, selenium and boron, as well as their oxides and volatile complexes which are liberated from the combustible liquid upon combustion. The apparatus may be employed to recover all of these elements. Since the chemical treating solution must be formulated to recover a preselected element listed in the specified group and placed in the recovery vessel prior to the initiation of combustion and using the apparatus, one must have selected a specific element to recover from the combustion gases.

The invention has been described with reference to its preferred embodiment. From this description, a person of ordinary skill in the art may appreciate changes that could be made in the invention which do not depart from the scope and spirit of the invention as described above and claimed hereafter.

What is claimed is:

1. An apparatus for the combustion of liquids and the recovery of a preselected element from gaseous combustion products, said preselected element selected from the group consisting of iodine, arsenic, mercury, phosphorous, selenium and boron, comprising:
   (a) a combustion chamber having an inlet for oxygen, an inlet for a combustible liquid, and an outlet for gaseous combustion products produced in said combustion chamber, said outlet in flow communication with a recovery vessel containing a chemical treating solution formulated to recover a preselected element from gaseous combustion products,
   (b) said combustion chamber further comprising a combustion dish, said dish in flow communication with the inlet for a combustible liquid and constructed so as to provide the combustible
   (c) said combustion chamber further comprising a means for igniting the combustible liquid within the combustion zone of the combustion dish to produce gaseous combustion products of the combustible liquid;
   (d) a means for continuously supplying oxygen, said oxygen supplying means in flow communication with the inlet for oxygen of said combustion chamber and combustion zone;
   (e) a means for continuously supplying the combustible liquid to said combustion dish, said liquid supplying means in flow communication with the inlet for a combustible liquid and the combustion dish; and
   (f) a means for intimately contacting the gaseous combustion products with the chemical treating solution to recover into the chemical treating solution the preselected element selected from the group consisting of iodine, arsenic, mercury, phosphorous, selenium and boron, said means for contacting in flow communication with the recovery vessel.

2. The apparatus of claim 1 wherein said combustion dish is funnel-shaped or inverted funnel-shaped.

3. The apparatus of claim 2, wherein the combustion dish has sides angularly sloped between about 90° and about 160°

4. The apparatus of claim 1, wherein the means for contacting is a sparger constructed so as to break the gaseous combustion products into bubbles of gas.

5. An apparatus for the combustion of liquids and the recovery of iodine from gaseous combustion products, comprising:
   (a) a combustion chamber having an inlet for oxygen, an inlet for a combustible liquid, and an outlet for gaseous combustion products produced in said combustion chamber, said outlet in flow communication with a recovery vessel containing a chemical treating solution formulated to recover iodine from gaseous combustion products,
   (b) said combustion chamber further comprising a funnel-shaped or inverted funnel-shaped combustion dish with sides angularly sloped between about 90° and about 160°, said dish in flow communication with the inlet for a combustible liquid and constructed so as to provide the combustible liquid to a combustion zone within the dish,
   (c) said combustion chamber further comprising a means for igniting the combustible liquid within the combustion zone of the combustion dish to produce gaseous combustion products of the combustible liquid;
   (d) a means for continuously supplying oxygen said oxygen supplying means in flow communication with said combustion chamber and combustion zone;
   (e) a means for continuously supplying the combustible liquid to said combustion dish, said liquid supplying means in flow communication with the inlet for a combustible liquid and the combustion dish; and
   (f) a sparger constructed so as to break the gaseous combustion products containing iodine into bubbles of ga for intimately contacting the bubbles of gas with the chemical treating solution formulated to recover iodine into the chemical treating solution, said sparger in flow communication with the recovery vessel.

6. An apparatus for the combustion of liquids and the recovery of a preselected element from gaseous combustion products, said preselected element selected from the group consisting of iodine, arsenic, mercury, phosphorous, selenium and boron, comprising:
   (a) a combustion chamber having an inlet for oxygen, an inlet for a combustible liquid, and an outlet for gaseous combustion products produced in said combustion chamber, said outlet in flow communication with a recovery vessel containing a chemical treating solution formulated to recover a preselected element from gaseous combustion products,
   (b) said combustion chamber further comprising a burner located in the combustion chamber in flow communication with the inlet for a combustible liquid, the inlet for oxygen, and the outlet for combustion products, said burner constructed so as to produce gaseous combustion products of the combustible liquid;
   (c) a means for continuously supplying oxygen, said oxygen supplying means in flow communication with the inlet for oxygen and the burner;
   (d) a means for continuously supplying the combustible liuqid to the burner, said liquid supplying means in flow communication with the inlet for a combustible liquid and the burner; and
   (f) a means for intimately contacting the gaseous combustion products with the chemical treating solution to recover into the chemical treating solution the preselected element selected from the group consisting of iodine, arsenic, mercury, phosphorous, selenium and boron, said means for contacting in flow communication with the recovery vessel.

* * * * *

UNITED STATES PATENT AND TRADEMARK OFFICE
CERTIFICATE OF CORRECTION

PATENT NO. : 5,141,713

DATED : August 25, 1992

INVENTOR(S) : David Gerard Nolte, Edwin Lee Colling, Jr. and Kadry Kaddis Bissada It is certified that error appears in the above-identified patent and that said Letters Patent is hereby corrected as shown below:

In Claim 1, Col. 7, line 16, after "combustible", please add --liquid to a combustion zone within the dish.--

In Claim 1, Col. 7, line 31, please delete "intimately".

In Claim 5, Col. 8, line 20, please substitute --gas-- for "ga".

Signed and Sealed this

Seventh Day of September, 1993

*Attest:*

BRUCE LEHMAN

*Attesting Officer*     *Commissioner of Patents and Trademarks*